United States Patent [19]
Ruske et al.

[11] Patent Number: 5,919,914
[45] Date of Patent: Jul. 6, 1999

[54] CLATHRATE OF BIS [6-HYDROXY-4-METHYL-5-(3-METHYL-IMIDAZOLIUM-1-YL) -3-(PHEN-4-YLAZO) PYRIDIN-2-ONE] ETHYLENE AND AN AROMATIC COMPOUND

[75] Inventors: Manfred Ruske, Ludwigshafen; Peter Erk; Heidi Hengelsberg, both of Frankenthal, all of Germany

[73] Assignee: BASF Aktiengesellschaft, Ludwigshafen, Germany

[21] Appl. No.: 09/042,808

[22] Filed: Mar. 17, 1998

[30] Foreign Application Priority Data

Mar. 19, 1997 [DE] Germany .................. 197 11 446

[51] Int. Cl.$^6$ .................. C09B 29/42; C09B 29/22; C09B 29/09; C09B 29/36
[52] U.S. Cl. .................. 534/608; 534/606; 534/607; 534/765; 534/775; 534/772; 546/187; 546/226
[58] Field of Search .................. 534/606, 607, 534/775, 757, 608, 765, 772; 546/187, 226

[56] References Cited

U.S. PATENT DOCUMENTS 5,424,404  6/1995  Ruske et al. .................. 534/606

FOREIGN PATENT DOCUMENTS 0 482 508 A1  4/1992  European Pat. Off. .

*Primary Examiner*—Floyd D. Higel
*Attorney, Agent, or Firm*—Oblon, Spivak, McClelland, Maier & Neustadt, P.C.

[57] ABSTRACT

Clathrates of bis[6-hydroxy-4-methyl-5-(3-methyl-imidazolium-1-yl)-3-(phen-4-ylazo)pyridin-2-one]ethylene with aromatics of the general formula I

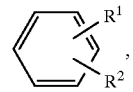

(I)

where $R^1$ is $C_1$–$C_5$-alkyl, $C_1$–$C_5$-hydroxyalkyl, $C_1$–$C_5$-alkoxy, $C_1$–$C_5$-hydroxyalkoxy, $C_1$–$C_{10}$-alkyl which is interrupted by 1, 2 or 3 non-neighboring oxygen atoms and is unsubstituted or substituted by hydroxyl, $C_1$–$C_{10}$-alkoxy which is interrupted by 1, 2 or 3 non-neighboring oxygen atoms and is unsubstituted or substituted by hydroxyl, or is $C_1$–$C_6$-alkanoyl, hydroxy, carboxyl, $C_1$–$C_6$-alkoxycarbonyl, phenylcarbonyl or $C_1$–$C_6$-alkenyl and $R^2$ is $R^1$, hydrogen or phenoxy, a process for their preparation and their use for the preparation of formulations of the dye.

9 Claims, No Drawings

CLATHRATE OF BIS [6-HYDROXY-4-METHYL-5-(3-METHYL-IMIDAZOLIUM-1-YL) -3-(PHEN-4-YLAZO) PYRIDIN-2-ONE] ETHYLENE AND AN AROMATIC COMPOUND

The present invention relates to clathrates, crystalline solvates, of bis[6-hydroxy-4-methyl-5-(3-methylimidazolium-1-yl)-3-(phen-4-ylazo)pyridin-2-one] ethylene with aromatics of the general formula I

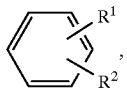

(I)

where $R^1$ is $C_1$–$C_5$-alkyl, $C_1$–$C_5$-hydroxyalkyl, $C_1$–$C_5$-alkoxy, $C_1$–$C_5$-hydroxyalkoxy, $C_1$–$C_{10}$-alkyl which is interrupted by 1, 2 or 3 non-neighboring oxygen atoms and is unsubstituted or substituted by hydroxyl, $C_1$–$C_{10}$-alkoxy which is interrupted by 1, 2 or 3 non-neighboring oxygen atoms and is unsubstituted or substituted by hydroxyl, or is $C_1$–$C_6$-alkanoyl, hydroxyl, carboxyl, $C_1$–$C_6$-alkoxycarbonyl, phenylcarbonyl or $C_1$–$C_6$-alkenyl and $R^2$ is $R^1$, hydrogen or phenoxy, a process for their preparation and their use for the preparation of formulations of the dye.

Cationic dyes are as a rule weak bases and therefore often poorly soluble in aqueous basic solvents. This is made use of in the synthesis of cationic azo dyes by rendering the dye solution obtained by acidic coupling alkaline, precipitating the dye and filtering it from the reaction solution. In EP-A-482 508, this procedure is described for the preparation of bis[6-hydroxy-4-methyl-5-(3-methylimidazolium-1-yl)-3-(phen-4-ylazo)pyridin-2-one]ethylene. However, the purification of this chromophore is not possible since a virtually unfilterable gel is obtained.

It is an object of the present invention to provide a crystalline form of the chromophore which permits purification.

We have found that this object is achieved by the abovementioned clathrates and a process for their preparation.

All alkyl groups occuring in the abovementioned formula I as radicals $R^1$ or $R^2$ may be either straight-chain or branched.

Suitable alkyl radicals preferably have 1, 2 or 3 substituents, in particular 1 or 2 substituents, in any position.

Alkyl radicals which are interrupted by oxygen atoms preferably have 1 or 2 oxygen atoms.

Where the stated radicals have two or more substituents, these may be identical or different.

Radicals $R^1$ and $R^2$ are, for example, methyl, ethyl, propyl, isopropyl, butyl, isobutyl, sec-butyl, tert-butyl, pentyl, isopentyl, neopentyl, tert-pentyl, methoxy, ethoxy, propoxy, isopropoxy, butoxy, pentyloxy, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7 dioxanonyl, 2- or 4-butoxybutyl, 4,8-dioxadecyl, 3,6,9-trioxadecyl, 3,6, 9-trioxaundecyl, hydroxymethyl, 2-hydroxyethyl, 2- or 3-hydroxypropyl, 2-hydroxyethyloxy, 2-(2-hydroxyethoxy) ethyl, 3-(2-hydroxyethoxy)propyl, 3-(4-hydroxybutoxy) propyl, formyl, acetyl, propionyl, butyryl, pentanoyl, hexanoyl, methoxycarbonyl, ethoxycarbonyl, propoxycarbonyl, isopropoxycarbonyl, butoxycarbonyl, pentyloxycarbonyl, hexyloxycarbonyl, vinyl or allyl.

Aromatics of the general formula I are generally known. These include commercial substances such as salicylic acid, phenol, resorcinol, 2-phenoxyethanol, phenylethanol, benzyl alcohol, toluene, acetophenone, benzoic acid, methyl benzoate, anisol, benzophenone, xylene, 4-methoxybenzyl alcohol, 4-methoxybenzaldehyde, 2-hydroxyacetophenone and 4-hydroxyacetophenone.

Hydroxybenzenes, hydroxyalkylbenzenes and benzenecarboxylic acids and their esters are preferred.

Clathrates with phenylethanol, resorcinol, toluene, phenol, methyl benzoate, salicylic acid, benzoic acid, acetophenone and in particular 2-phenoxyethanol or benzyl alcohol as the intercalated solvent are particularly preferred.

The novel clathrates are obtained by treating the aqueous dye solution with one or more aromatics of the general formula I under basic conditions. The clathrates are preferably prepared by addition of a single aromatic I. The aqueous solution obtained directly by acidic azo coupling is advantageously reacted under basic conditions.

Basic conditions is to be understood as meaning a pH of 8–14, preferably 10–13, which is achieved by means of conventional bases. Clathrates are obtainable in the adjacent neutral range to pH 6, but in lower yields. Suitable inorganic bases are the hydroxides, oxides and basic salts of alkali metals and alkaline earth metals, such as sodium hydroxide, potassium hydroxide, sodium oxide, potassium oxide, magnesium oxide, potassium carbonate, magnesium carbonate, lithium carbonate and sodium carbonate.

The order of addition of base and aromatic to the resulting clathrates has no effect. However, since on the addition of a base some of the dye separates off as a gel, it is advantageous to add the aromatic compound first.

The formation of the clathrates takes place at as low as room temperature. The formation process can however be accelerated and improved by heating, preferably to 40–100° C., particularly preferably 70–90° C. Heating promotes the formation of readily filterable crystals.

A heating period of more than 30 min is sufficient to obtain good results. As a rule, heating is carried out over a period of from 1 to 4 hours in order to optimize the yield. Longer heating periods have no noticeable effect on the completeness of the conversion.

A uniform thorough mixing, for example by stirring, is advantageous but not necessary.

1 mol of dye is as a rule reacted with at least an equimolar amount, preferably up to 3.5 times the molar amount, of aromatic of the formula I. Preferably 1.4–2.5, in particular 1.6–2.1, mol of an aromatic I are chosen per mole of dye. A larger excess, for example 5 mol, has no effect on the composition of the clathrate since presumably only 1:1 clathrates are formed and hence a fixed number of voids are available in the crystal framework. In any case, dissolving the dye in the aromatic of the formula I results in an upper limit. Smaller amounts, for example 0.8 mol, result in incomplete intercalation, ie. defects, but crystalline structures still form. Different molar ratios can result in different crystal modifications, which however are just as easy to handle.

The dye concentration affects the clathrates being formed only in that high dilutions slow down the reaction. In a preferred embodiment, the clathrates are formed starting from a 2–10% strength by weight aqueous dye solution.

In a preferred embodiment, the 2–10% strength by weight aqueous dye solution obtained by acidic coupling is reacted with an equimolar amount to 3.5 times the molar amount of an aromatic of the formula I and the pH is then brought to 8–14 with an inorganic base. The mixture is then heated at 40–100° C. for 0.5–5 hours. After cooling to room temperature, the crystals are separated off, for example by filtration or centrifuging, and are washed, preferably with water.

Since the clathrates of a dye which is cationic owing to its imidazolium radicals are prepared under basic conditions, it is presumably present in the crystal with an opposite ion, in this case $OH^{\ominus}$. However, it would also be possible for the dye to have a betaine structure in the case of the crystals obtainable by the process described above.

After cooling, the novel clathrates can be readily filtered and washed. They are suitable for the preparation of a liquid formulation of the dye. The crystalline form permits controlled metering and the preparation of concentrated stable formulations, as described, for example, in EP-A-482 508. Further, they are suitable for the preparation of granules or powders.

The novel clathrates give pure and brilliant dyeings having good fastness properties in the dyeing or printing of polymeric material. The latter is to be understood as meaning cellulose, cotton, leather, bast fibers, hemp, flax, sisal, jute, coconut fibers, straw and especially paper stocks. Exact information on the use is given in EP-A-482 508 with respect to the chromophore and is of course applicable to the clathrates.

The examples which follow illustrate the invention.

EXAMPLE 1

100 g of ice were added to a mixture consisting of 10.6 g (0.05 mol) of 4,4'-diaminodibenzyl, 123.4 g of water and 26 g of 38% by weight hydrochloric acid (0.27 mol of HCl) and tetrazotization was carried out at 0–5° C. with 30 ml of a 23% strength by volume (0.1 mol of sodium nitrite) sodium nitrite solution. The cold solution was then added dropwise to an aqueous solution of 24.1 g (0.1 mol) of 3-(N-methylimidazolium)-4-methyl-6-hydroxy-2-pyridone chloride in 270 g of water. The temperature was kept at 0–10° C. by adding 50–100 g of ice and the pH was kept at 3–5 by adding dilute aqueous sodium hydroxide solution. After complete coupling, 11 g (0.08 mol) of 2-phenoxyethanol were added at room temperature and the pH was brought to 10–12 with dilute sodium hydroxide solution. The mixture was then heated to 70–90° C. and was stirred for a further 1–2 hours at this temperature. After cooling, the precipitate was filtered off. The press cake showed very good suction and wash properties.

In the X-ray diffraction pattern (Cu—Kα radiation) of the crystals, lines were obtained at the following diffraction angles 2Θ(°):

7.1; 8.4; 8.7; 9.6; 10.6; 11.7; 14.2; 14.4; 15.4; 16.8; 17.3; 17.7; 19.2; 20.7; 21.2; 22.4; 23.5; 24.8; 25.1; 25.3; 26.1; 26.9; 27.3; 27.9; 28.4; 29.0; 29.4; 30.1.

Elemental analysis for the 1:1 clathrate of 2-phenoxyethanol and the dye as bishydroxide: $C_{42}H_{46}N_{10}O_8$; calculated: C 61.60 H 5.66 N 17.10 O 15.63; found: C 60.9 H 5.8 N 17.3 O 16.0

The solution of the clathrate in 30% strength by weight acetic acid has an absorption maximum ($\lambda_{max}$) of 442 nm and colors paper in greenish yellow hues.

Clathrates having good suction and wash properties were obtained similarly to Example 1 with the aromatics shown in the table below:

| Example | Aromatic I | Amount [g] |
|---------|------------|------------|
| 2 | Benzyl alcohol | 15 |
| 3 | Phenylethanol | 10 |
| 4 | Resorcinol | 5.8 |
| 5 | Toluene | 11 |
| 6 | Phenol | 11 |
| 7 | Methyl benzoate | 5.8 |
| 8 | Salicylic acid | 11 |
| 9 | Benzoic acid | 11.6 |
| 10 | Acetophenone | 11 |
| 11 | Phenylethanol | 20 |

2 Theta values for Example 2:
7; 8.3; 8.5; 9.5; 10.5; 11.6; 14.1; 14.4; 15.3; 16.7; 17.2; 17.6; 19.1; 20.6; 21.1; 22.4; 23; 24.8; 26.1; 26.9

Elemental analysis for the 1:1 clathrate of benzyl alcohol and the dye as bishydroxide: $C_{41}N_{10}O_7$; calculated: C 62.43 H 5.62 N 17.76 O 14.20; found: C 62.2 H 5.6 N 17.9 O 14.5

2 Theta values for Example 3:
6.8; 8.0; 8.3; 8.7; 9.2; 10.2; 11.2; 12.4; 13.6; 14.8; 16.0; 16.8; 19.1; 19.9; 21.2; 22.5; 23.3; 25.3; 26.7; 27.9.

2 Theta values for Example 6:
4.9; 6.2; 7.9; 9.7; 9.9; 12; 12.5; 12.9; 13.5; 15; 15.6; 15.9; 16.3; 17.4; 17.8; 19.1; 19.5; 19.6; 19.9; 20.1; 21.4; 22.2; 23.3; 25.5; 28.3.

2 Theta values for Example 8:
7.2; 7.6; 8.9; 9.1; 9.3; 11.6; 13.8; 14.6; 14.9; 15.3; 16; 16.6; 17.8; 18.3; 18.7; 19.2; 22.8; 24.1; 27; 28; 28.4.

2 Theta values for Example 10:
3.1; 6.2; 7.9; 8.2; 8.4; 8.7; 9.3; 10; 10.6; 11.7; 13.2; 14.2; 15.5; 15.8; 16; 16.8; 18.7; 19.9; 20.6; 21.7; 24.1; 25.1.

2 Theta values for Example 11:
3.4; 6.7; 7; 7.9; 8.4; 8.6; 9.4; 10; 10.4; 11.5; 13.3; 13.9; 15.9; 16.8; 18.8; 20.1; 21; 21.9; 25.1; 26.8.

We claim:

1. A clathrate of bis[6-hydroxy-4-methyl-5-(3-methylimidazolium-1-yl)-3-(phen-4-ylazo)pyridin-2-one]ethylene with an aromatic compound of the formula I

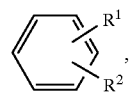

(I)

where
$R^1$ is $C_1$–$C_5$-alkyl, $C_1$–$C_5$-alkoxy, $C_1$–$C_5$-hydroxyalkyl, $C_1$–$C_5$-hydroxyalkoxy, $C_1$–$C_{10}$-alkyl which is interrupted by 1, 2 or 3 non-neighboring oxygen atoms and is unsubstituted or substituted by hydroxyl, $C_1$–$C_{10}$-alkoxy which is interrupted by 1, 2 or 3 non-neighboring oxygen atoms and is unsubstituted or substituted by hydroxyl, or is $C_1$–$C_6$-alkanoyl, hydroxyl, carboxyl, $C_1$–$C_6$-alkoxycarbonyl, phenylcarbonyl or $C_1$–$C_6$-alkenyl and
$R^2$ is $R^1$, hydrogen or phenoxy.

2. A clathrate as claimed in claim 1, wherein said aromatic compound is 2-phenoxyethanol or benzyl alcohol.

3. A process for the preparation of a clathrate as claimed in claim 1, wherein an aqueous dye solution of said imidazolium-1-yl salt compound is reacted with an aromatic compound of formula I under basic conditions.

4. A process as claimed in claim 3, wherein one mole of dye is reacted with from 1 to 3.5 mol of the aromatic compound of the formula I.

5. A process as claimed in claim 3 or 4, wherein a basic pH is established after the addition of the aromatic compound of the formula I.

6. A process for the preparation of a clathrate as claimed in claim 3, wherein the mixture of dye and aromatic compound of formula I is heated to 40–100° C.

7. A method for the preparation of liquid formulations of bis[6-hydroxy-4-methyl-5-(3-methylimidazolium-1-yl)-3-(phen-4-ylazo)pyridin-2-one]ethylene, comprising:

isolating a clathrate as claimed in claim 1 and dissolving the clathrate in a liquid.

8. A method for the preparation of dye granules or powders, comprising:

isolating the clathrate as claimed in claim 1;

dissolving the clathrate in a liquid; and drying the clathrate.

9. A method for dyeing or printing polymeric material, comprising:

dyeing or printing the polymeric material with the clathrate as claimed in claim 1.

* * * * *